(12) United States Patent
Bartus et al.

(10) Patent No.: US 8,420,619 B2
(45) Date of Patent: *Apr. 16, 2013

(54) RESCUE OF PHOTORECEPTORS BY INTRAVITREAL ADMINISTRATION OF AN EXPRESSION VECTOR ENCODING A THERAPEUTIC PROTEIN

(75) Inventors: Raymond T. Bartus, San Diego, CA (US); Kathie M. Bishop, San Diego, CA (US); Mehdi Gasmi, San Diego, CA (US)

(73) Assignee: Ceregene, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/212,078

(22) Filed: Aug. 17, 2011

(65) Prior Publication Data

US 2012/0316112 A1    Dec. 13, 2012

Related U.S. Application Data

(62) Division of application No. 12/366,596, filed on Feb. 5, 2009, now Pat. No. 8,242, 093.

(60) Provisional application No. 61/026,990, filed on Feb. 7, 2008, provisional application No. 61/093,228, filed on Aug. 29, 2008.

(51) Int. Cl.
*A61K 48/00* (2006.01)

(52) U.S. Cl.
USPC ..................... 514/44 R; 424/93.21

(58) Field of Classification Search ............... 514/44 R; 424/93.21
See application file for complete search history.

(56) References Cited

U.S. PATENT DOCUMENTS

| 6,642,053 | B1 | 11/2003 | Daniell et al. |
| 7,354,760 | B2 | 4/2008 | Daniell |
| 8,242,093 | B2 * | 8/2012 | Bartus et al. ............ 424/93.21 |
| 2002/0194630 | A1 * | 12/2002 | Manning et al. ............ 800/8 |
| 2005/0208103 | A1 | 9/2005 | Adamis et al. |
| 2006/0188481 | A1 | 8/2006 | Mori |

FOREIGN PATENT DOCUMENTS

| WO | WO 01/64850 | 9/2001 |
| WO | WO 01/72959 | 10/2001 |
| WO | WO 2004/005467 | 1/2004 |
| WO | WO 2006/101634 A1 | 9/2006 |
| WO | WO 2006/104609 A2 | 10/2006 |
| WO | WO 2007/053183 | 5/2007 |

OTHER PUBLICATIONS

Jomary et al., "Epitope-tagged recombinant AAV vectors for expressing neurturin and its receptor in retinal cells", *Mol. Vis.*, 7:36-41 (2001).

Peterson et al., "Enhanced survival of photoreceptors in P23H mutant rhodopsin transgenic rats by adeno-associated virus (AAV)-mediated delivery of neurotrophis genes", *Invest. Ophthalmol. Vis Sci.*, 39:S1117 (1998) Abstract.

European Search Report from EP 09 70 7354.

* cited by examiner

*Primary Examiner* — Anne Marie S Wehbe
(74) *Attorney, Agent, or Firm* — DLA Piper LLP (US)

(57) ABSTRACT

The invention provides methods for treating ocular diseases using a recombinant vehicle to express a protein useful in the treatment of ocular disease, with particular preference for use of neurotrophin-4 (NT4) for targeting subpopulations of cells in the retina. A genetically engineered gene transfer vector containing sequences encoding a growth factor such as neurotrophin-4 (NT4) is used to transduce cells of the retinal ganglion cell (RGC) layer, in situ, via administration of the vector intravitreally. Accordingly, methods are disclosed for treating subjects in need thereof by therapeutic protein delivery via a recombinant expression vector, including rescue of photoreceptors by targeting the RGC layer subpopulation of retinal cells.

10 Claims, 14 Drawing Sheets

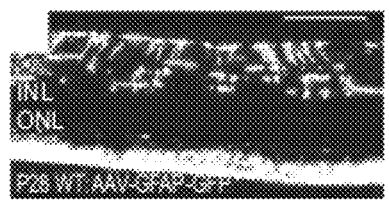
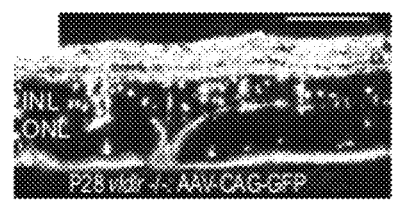
FIG. 12A    FIG. 12B
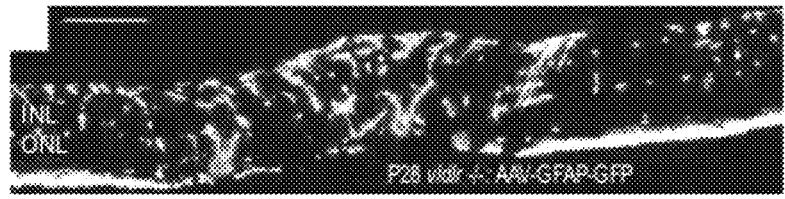
FIG. 12C
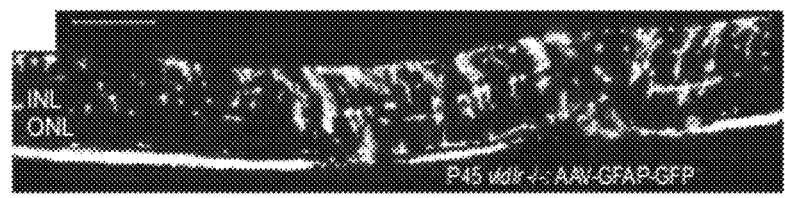
FIG. 12D
FIG. 12E
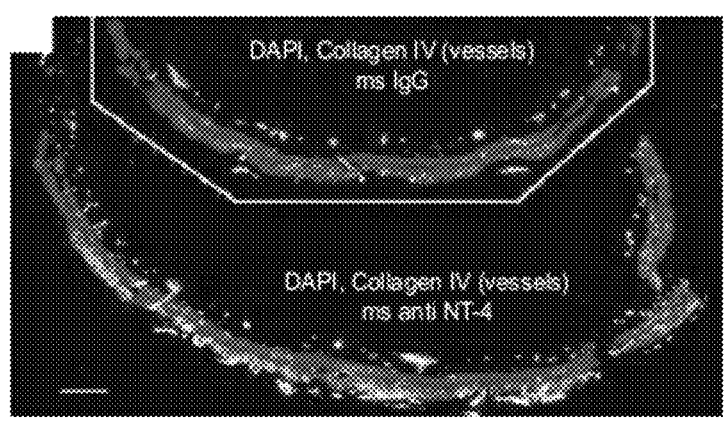
FIG. 12F ERG measurements in 4-month-old WT and untreated, AAV-GFAP-GFP control-treated, and AAV-GFAP-NT4-treated Vldlr-/- mice 3.5 months after injection

| Stimulus | Measurement | WT (n=12) | Vldlr-/- untreated (n=10) | Vldlr-/- GFP (n=15) | Vldlr-/- NT4 (n=15) | P (NT4 vs. GFP) |
|---|---|---|---|---|---|---|
| Scotopic measurements | | | | | | |
| Low intensity[B] | B-wave implict time (ms) | 121 ± 5 | 130 ± 4 | 126 ± 4 | 118 ± 2 | 0.005[H] |
| High intensity[C] | A-wave amplitude (μV) | 136 ± 25 | 80 ± 17 | 68 ± 13 | 114 ± 18 | 0.01[H] |
| High intensity | A-wave implict time (ms) | 24 ± 1 | 24 ± 1 | 24 ± 1 | 22 ± 1 | 0.067 |
| High intensity | B-wave amplitude (μV) | 80 ± 4 | 89 ± 2 | 93 ± 4 | 75 ± 2 | 0.0002[H] |
| Maximum OP[D] | Amplitude (μV) | 71 ± 10 | 39 ± 7 | 36 ± 7 | 62 ± 12 | 0.013[H] |
| Photopic measurements[E] | | | | | | |
| 1 Hz[F] | A-wave implict time (ms) | 19 ± 2 | 23 ± 1 | 22 ± 1 | 18 ± 1 | 0.005[H] |
| 1 Hz | B-wave amplitude (μV) | 105 ± 9 | 83 ± 6 | 80 ± 11 | 96 ± 9 | 0.022[H] |
| 1 Hz | B-wave implict time (ms) | 62 ± 4 | 71 ± 3 | 78 ± 3 | 58 ± 2 | 0.000[H] |
| 16 Hz flicker[G] | Amplitude (μV) | 19 ± 3 | 16 ± 2 | 15 ± 2 | 19 ± 2 | 0.041[H] |
| 16 Hz flicker | Implicit time (ms) | 55 ± 3 | 58 ± 1 | 58 ± 1 | 56 ± 1 | 0.175 |

Values are mean ±SEM. [A]Dark-adapted measurements performed to determine rod and mixed cone-rod function. [B]0.005 cd·s/m². [C]2 cd·s/m². [D]10 cd·s/m². [E]Light-adapted measurements performed to determine cone function. [F]20 cd·s/m². [G]10 cd·s/m². [H]Statistically significant difference between contro-laterally AAV-GFAP-NT4- and AAV-GFAP-GFP-treated eyes.

FIG. 12J

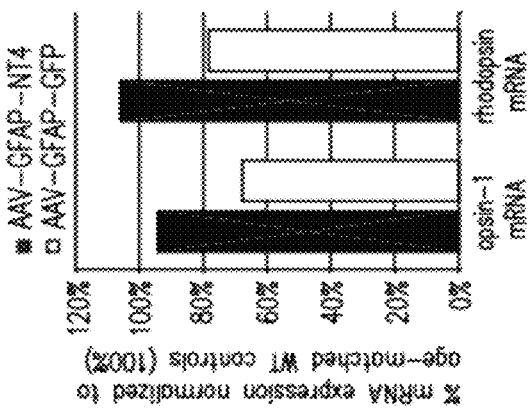

FIG. 12G

RESCUE OF PHOTORECEPTORS BY INTRAVITREAL ADMINISTRATION OF AN EXPRESSION VECTOR ENCODING A THERAPEUTIC PROTEIN

CROSS REFERENCE TO RELATED APPLICATION(S)

This application is a divisional application of U.S. application Ser. No. 12/366,596, filed Feb. 5, 2009 now U.S. Pat. No. 8,242,093, which claims the benefit of priority under 35 U.S.C. §119(e) of U.S. Ser. No. 61/026,990, filed Feb. 7, 2008 and of U.S. Ser. No. 61/093,228, filed Aug. 29, 2008, the entire contents of each is incorporated herein by reference.

BACKGROUND OF THE INVENTION

1. Field of the Invention

The invention relates generally to ocular therapy and, more specifically to methods of treating and preventing photoreceptor degradation by supplying specific subpopulations of the retina with a therapeutic protein, preferably human neurotrophin 4 (NT4), using a recombinant delivery vehicle to target and express the neurotrophic growth factor.

2. Background Information

Retinitis pigmentosa (RP) is a term that refers to group of hereditary disorders that affect the retina's ability to respond to light. While in most cases the disease appears to be autosomal recessive, it may also be autosomal dominant or, infrequently, X linked, and may occur as a part of a syndrome complex. Patients with RP have night blindness in adolescence followed by complete loss of vision in adulthood.

RP primarily affects rod cells, the photoreceptor cell that is responsible for night vision, seeing in dim light, and peripheral vision. Cone cells, which are responsible for color vision and seeing in bright light, may also be affected as the disease progresses.

Rhodopsin is a photosensitive eye pigment found exclusively in rods of the eye. In individuals with the autosomal dominant form of RP, the rhodopsin gene comprises a single nucleotide change. The mutant gene underlies abnormal light-evoked responses from the retina in otherwise presymptomatic individuals and eventually leads to progressive degeneration of both rod and cone photoreceptor cells. The precise mechanism of degeneration is unknown, but may result from the gradual accumulation of undegraded mutant rhodopsin and abnormal membranous discs in the rod cells, with secondary responses of the retina to this malformation.

Neurotrophins are known to play key roles in the survival and differentiation of select neurons in the peripheral and central nervous system (e.g., nerve growth factor (NGF); brain-derived neurotrophic factor (BDNF); and neurotrophin-4 (NT4)). These factors have been shown to act on cells belonging to the visual system. Receptors for these factors are expressed in the retina. Some of these factors may be transported in an anterograde fashion along RGC axons, which together comprise the optic nerve.

In many CNS regions, developing neurons and their connections are overproduced and then partially eliminated. In normal rodents, ~65% of developing RGCs die by pyknosis. Immature periphery sensory and sympathetic neurons survive by competing for target derived neurotrophins. While the survival-promoting effects of neurotrophins on developing CNS neurons is controversial, neurotrophins have been shown to promote survival of these neurons in vitro, and have been shown to slow or reduce axotomy-induced death of CNS neurons, including developing and mature RGCs.

Accordingly, previous studies have shown that growth factors can rescue dying photoreceptor cells. For example, eight different factors when injected into the retina of rats exposed to constant high intensity light, all showed the ability to delay the degeneration of photoreceptor cells. These include FGF (both acidic and basic forms), BDNF, ciliary neurotrophic factor (CNTF), and interleukin 1 (IL-1). Neurotrophin 3 (NT-3), insulin like growth factor II (IGF-II), transforming growth factor beta (TGF-$\beta$) and the tumor necrosis factors alpha and beta (TNF-$\alpha$, TNF-$\beta$) also showed survival activity, but to a much lesser degree than the other factors. However, direct injection of these protein factors is insufficient for long term treatment and maintenance of photoreceptor function.

Recent work has shown that the retinal degeneration phenotype of the rd mouse, which has served as a model for the study of RP for over 30 years, may be rescued by the expression of bovine cGMP phosphodiesterase $\beta$-subunit in transgenic mice. Similarly, the retinal degeneration slow (rds) phenotype of the rds mouse may also be corrected by the creation of transgenic mice expressing the wild-type rds gene product, a 39 kDa membrane associated glycoprotein. However, transgenic techniques are not directly applicable to human therapy.

Therefore, there remains a need for sustained in vivo and in situ delivery of neurotrophins in therapies for treating various ocular conditions.

SUMMARY OF THE INVENTION

The present invention relates to a method of treating ocular diseases by rescuing photoreceptors of the eye using a recombinant vehicle to express a neurotrophic factor for targeting subpopulations of cells in the retina. Using a genetically engineered gene transfer vector containing sequences encoding a nerve growth factor (preferably neurotrophin-4 (NT4)), the retinal ganglion cell (RGC) layer is specifically transduced in situ by the vector when administered intravitreally, or said RGC layer is impacted by expression of a growth factor following intravitreal implantation of a donor cell transduced with an expression vector encoding the growth factor. Accordingly, methods are disclosed for treating subjects in need thereof using this vector, including rescuing photoreceptors by targeting the RGC layer subpopulation of cells.

In one embodiment, a method of rescuing photoreceptors of the eye in situ is disclosed including infecting retinal ganglion cells (RGC) of the retina with an expression vector that operatively encodes a growth factor, where the vector is administered to the RGC by intravitreal injection into the eye, and further the infected cells constitutively express the growth factor. In a related aspect, the expression vector may be delivered in a suitable donor cell that is implanted into the eye for intravitreal expression of the growth factor.

In a related aspect, the method includes the administration of a second growth factor or calcium channel blocker. In another related aspect, the second growth factor is brain derived neurotrophic factor (BDNF), glial-cell line derived neurotrophic factor (GDNF) or ciliary neurotrophic factor (CNTF). In a further related aspect, the second nerve growth factor is delivered intravitreally or subretinally, as a protein, via in vivo delivery of a growth factor encoding recombinant expression vector, or as recombinantly expressed from a genetically engineered donor cell.

In one aspect, the growth factor is NT4. In yet another aspect, the expression vector is an AAV vector derived from adeno-associated virus. In another aspect, the AAV vector is AAV type 2 (AAV2), or another AAV serotype with tropism for ocular cells. In a further aspect, neighboring cells are activated via RGC infection, where such neighboring cells include, but are not limited to, rod photoreceptors, cone photoreceptors, bi-polar cells, horizontal cells, retinal pigmented epithelial cells, and Müller glia cells.

In one aspect, the method increases the amplitude of scotopic b-waves, scotopic a-waves, and/or photopic b-waves associated with photoreceptor degeneration in an ocular disease. In a related aspect, the ocular disease retinitis pigmentosa (including Usher Syndrome, Bardet-Biedl syndrome, Refsum disease), Leber congenital amaurosis, macular degeneration (including wet and dry forms of age-related macular degeneration, and Stargardt disease), vitelliform macular dystrophy (including Best disease), choroideremia, retinoschisis, cone-rod dystrophy, rod-cone dystrophy, malattia Leventinese (or Doyne honeycomb choroiditis), retinal angiomatous proliferation (RAP), macular telangiectasia (MacTel), or retinitis punctata alescens.

In another aspect, the method increases outer nuclear layer (ONL) thickness throughout the retina. In a related aspect, the increase in the thickness of the ONL layer is significant compared to a control.

In one aspect, the increase in the thickness of the ONL layer is significant compared to the response to infection of photoreceptor cells with the AAV vector by subretinal injection. In a related aspect, the infected RGC induce a paracrine response by neighboring cells.

In another aspect, the expression vector is derived from an AAV serotype with tropism for ocular tissue, wherein the vector is devoid of viral protein encoding sequences, but includes nucleic acid sequences encoding NT4. In a related aspect, the NT4 gene is flanked by AAV inverted terminal repeats (ITR).

In another embodiment, a method of treating oxidative damage to photoreceptors in situ is disclosed including administering an infective recombinant expression vector that operatively encodes a growth factor under a tissue specific promoter, where the vector is administered intravitreally to the eye of a subject, and upon infection, growth factor expression is substantially restricted to at least one selected tissue in the eye.

In one aspect, the growth factor is NT4. In another aspect, NT4 expression is substantially directed to the inner retina or the outer retina or a combination thereof, especially Müller glia cells, through use of a tissue specific promoter. In a related aspect, the vector includes a glial fibrillary acidic protein (GFAP) promoter, which has been found to be specific for retinal cells, especially Müller glia. In another aspect, the method further comprises co-administering at least one anti-angiogenic agent with the growth factor (e.g., NT4).

DETAILED DESCRIPTION OF THE INVENTION

Figure 1:
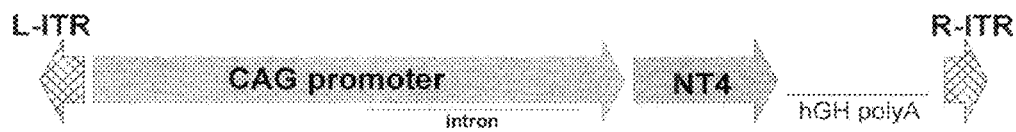
FIG. 1 shows a schematic illustration of the CERE-140 vector construct.

Before the present compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a vector" includes a plurality of such vectors, a reference to a "neurotrophin" is a reference to one or more neurotrophins and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Colowick, S. et al., eds., Methods In Enzymology, Academic Press, Inc.; Handbook of Experimental Immunology, Vols. I-IV (D. M. Weir and C. C. Blackwell, eds., 1986, Blackwell Scientific Publications); Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press); PCR (Introduction to Biotechniques Series), 2nd ed. (Newton & Graham eds., 1997, Springer Verlag).

The invention discloses a method for delivery of an exogenous nucleic acid encoding a growth factor, preferably NT4, for treatment of ocular cells, and in particular in situ delivery. Surprisingly, at least one other growth factor known to be useful in other contexts for treatment of nervous system disease, neurturin (NTN), did not prove as effective in the methods of the invention. Thus, the preferred methods provided for treating ocular cells utilize a genetically-engineered vector for delivery of NT4 in situ. This method comprises contacting an ocular cell with vector comprising a nucleic acid which encodes NT4 under conditions that allow the ocular cell to take up the exogenous nucleic acid into said ocular cell and express it. In one embodiment, the vector is delivered to an RGC layer via intravitreal injection.

Alternatively, the growth factor may be delivered by expression from a donor cell that has been transformed with an expression vector that encodes a growth factor; e.g., NT4. In one embodiment, the growth factor is delivered to an RGC layer via intravitreal implantation of the donor cells.

While not being bound by theory, it is reasonable to assume that the functional and anatomical benefits provided by growth factor encoding expression vectors according to the invention (e.g., AAV/NT4) are due to the bioactivity of the growth factor, and especially NT4, since NT4 protein has been shown to rescue photoreceptors in the constant light damage model. In contrast, other growth factors (including BDNF, bFGF, CNTF, and GDNF) have also demonstrated efficacy in several in vivo models of photoreceptor degeneration. Again, not to be bound by theory, one possible explanation for the improved efficacy seen following intravitreal AAV/NT4 over the subretinal route is that targeting the intravitreal space, and the RGC layer especially, is a more effective way to release NT4 within the retina. The latter hypothesis would likely support a paracrine mechanism whereby the viability of photoreceptors is ultimately preserved through one or more second messenger molecules. As such, delivery of the nerve growth factor encoding expression vector to the intravitreal space at a distance from the photoreceptors (i.e., within the intravitreal humor but at an anterior point therein) to maximize the number of intervening cell types that may be affected by growth factor triggering of a paracrine cascade is desirable.

By the term "in situ ocular cell" or grammatical equivalents herein is meant an ocular cell contained within the eye, i.e. in vivo. Ocular cells include cells of the lens, the cornea (both endothelial, stromal and epithelial corneal cells), the iris, the retina, choroid, sclera, ciliary body, vitrous body, ocular vasculature, canal of Schlemm, ocular muscle cells, optic nerve, and other ocular sensory, motor and autonomic nerves. In a preferred embodiment, the ocular cell is comprised in the retinal ganglion cell layer.

By the term "genetically-engineered" herein is meant a nucleic acid vehicle that has been subjected to recombinant DNA manipulations, such as the introduction of an exogenous nucleic acid or transgene, resulting in a nucleic acid vehicle that is in a form not ordinarily found in nature. Generally, the exogenous nucleic acid or transgene is made using recombinant DNA techniques. It is understood that once a genetically engineered vehicle is made, it may replicate non-recombinantly, i.e., using the in vivo cellular machinery of a host cell, but will still be considered genetically-engineered for the purposes of the invention. Also, in the case of a donor cell, such a cell is considered to have been genetically engineered when transduced with an exogenous nucleic acid, especially a recombinant expression vector.

By the term "nucleic acid" or grammatical equivalents herein is meant either DNA or RNA, or molecules which contain both ribo- and deoxyribonucleotides. The nucleic acids include genomic DNA, cDNA and oligonucleotides including sense and anti-sense nucleic acids. The nucleic acid may be double stranded, single stranded, or contain portions of both double stranded or single stranded sequence.

By the term "exogenous nucleic acid" or "foreign nucleic acid" or "recombinant nucleic acid" or grammatical equivalents herein is meant nucleic acid which encodes proteins not ordinarily made in appreciable or therapeutic amounts in ocular cells. Thus, exogenous nucleic acid includes nucleic acid which is not ordinarily found in the genome of the ocular cell, such as heterologous nucleic acid from other organisms. Exogenous nucleic acid also includes nucleic acid which is ordinarily found within the genome of the ocular cell, but is in a form which allows for the expression of proteins which are not ordinarily expressed in ocular cells in appreciable or therapeutic amounts. Alternatively, the exogenous nucleic acid may encode a variant or mutant form of a naturally-occurring protein.

It is understood that once an exogenous nucleic acid is made and reintroduced into a host cell or organism, it will replicate non-recombinantly, i.e. using the in vivo cellular machinery of the in situ host cell or donor cell rather than in vitro manipulations; however, such nucleic acids, once produced recombinantly, although subsequently replicated non-recombinantly, are still considered "exogenous" or "recombinant" for the purposes of the invention.

In one embodiment, the exogenous nucleic acid encodes a protein to be expressed. That is, it is the protein which is used to treat the ocular disease.

In one embodiment, the exogenous nucleic acid encodes a single protein. In alternative embodiments, the exogeneous nucleic acid encodes more than one protein. Thus, for example, several proteins which are useful to treat an ocular disorder may be desirable; alternatively, several ocular diseases may be treated at once using exogenous nucleic acid encoding several proteins.

Similarly, an "exogenous" or "recombinant protein" is a protein made using recombinant techniques, i.e., through the expression of an exogenous or recombinant nucleic acid as described above. A recombinant protein is distinguished from naturally occurring protein by at least one or more characteristics. For example, the protein may be made at a significantly higher concentration than is ordinarily seen, through the use of a inducible promoter or high expression promoter, such that increased levels of the protein is made. Thus, for instance, an exogenous protein is one which is not ordinarily expressed in ocular tissue. Alternatively, the protein may be in a form not ordinarily found in nature, as in the addition of an epitope tag or amino acid substitutions, insertions and deletions.

In a preferred embodiment, the exogenous nucleic acid encodes a protein useful in the treatment of ocular diseases. The protein is a growth factor that is expressed by the exogenous nucleic acid. The growth factor expression provided is transient or constitutive. Thus, for example, transient expression systems may be used when therapeutic proteins are to be delivered for a short period; for example, certain exogenous proteins are desirable after ocular surgery or wounding. Alternatively, for on-going or congenital ocular diseases, such as retinitis pigmentosa or macular degeneration, constitutive expression may be desired.

By "ocular disease" herein is meant a disorder or pathological condition of the eye which is not normal to the animal in a healthy state, whether as the result of a genetic defect, injury or other trauma (e.g., post-surgical conditions), disease or other disorder. Art-accepted animal models of such ocular diseases are known; for example, the retinal degeneration phenotype of the rd mouse has served as a model for the study of human retinitis pigmentosa for over 30 years (Lem et al., *Proc. Natl. Acad. Sci. USA.*, 15:442 (1992)). Other experimental protocols for generating and repairing retinal damage in animal models are exemplified herein.

In one embodiment, the ocular disease may be caused by a genetic defect. Examples of such ocular diseases for which a gene has been identified include, but are not limited to, autosomal retinitis pigmentosa, autosomal dominant retinitis punctata albescens, butterfly-shaped pigment dystrophy of the fovea, adult vitelliform macular dystrophy, Norrie's disease, blue cone monochromasy, choroideremia and gyrate atrophy. These may also be referred to as genetic ocular diseases.

In other embodiments, the ocular disease may not be caused by a specific known genotype (although they may be shown in the future to have a genetic component). These ocular diseases include, but are not limited to, macular degeneration, retinoblastoma, anterior and posterior uveitis, retinovascular diseases, cataracts, inherited corneal defects such as corneal dystrophies, retinal detachment and degeneration and atrophy of the iris, and retinal diseases which are secondary to glaucoma and diabetes, such as diabetic retinopathy.

In addition, the term ocular disease includes conditions which are not genetically based but still cause ocular disorders or dysfunctions. These include, but are not limited to, viral infections such as Herpes Simplex Virus or cytomegalovirus (CMV) infections, allergic conjunctivitis and other ocular allergic responses, dry eye, lysosomal storage diseases, glycogen storage diseases, disorders of collagen, disorders of glycosaminoglycans and proteoglycans, sphinogolipodoses, mucolipidoses, disorders of amino acid metabolism, dysthyroid eye diseases, anterior and posterior corneal dystrophies, retinal photoreceptor disorders, corneal ulceration, Usher syndrome, Bardet-Biedl syndrome, Refsum disease, Leber congenital amaurosis, macular degeneration, including, but not limited to wet and dry forms of age-related macular degeneration, Stargardt disease, vitelliform macular dystrophy, including but not limited to Best disease, choroidermia, retinoschisis, cone-rod dystrophy, rod-cone dystrophy, malattia Leventinese or Doyne honeycomb choroiditis, retinitis punctata alescens, and ocular wounds such as those following surgery or those abnormalities caused by oxidative stress/damage, such as retinal angiomatous proliferation (RAP) and macular telangiectasia (MacTel).

By the term "oxidative damage" or "oxidative stress" herein is meant a condition of increased oxidant production in a cell characterized by the release of free radicals and resulting in cellular degeneration. Oxidative stress is correlated with excessive neovascularization and is commonly associated with the pathogenesis of certain neurons, including retinal cone photoreceptors. In disorders associated with abnormal retinal angiogenesis, such as diabetic retinopathy, abnormal vessels can grow from the inner retina into the vitreous. In a common form or retinal neovascularization, called macular telangiectasia (or idiopathic parfoveal talangiectasia), intraretinal talangectatic vessels proliferate in the central portion of the inner retina and may grow into the normally avascular outer retina. In age-related macular degeneration (AMD), abnormal vessels typically arise from the choroid and invade the subretinal space. However, in a subset of patients with AMD, intraretinal and subretinal neovascularization arises from the inner retinal vessels, a condition known as retinal angiomatous proliferation (RAP).

In one embodiment, a method of treating disease or damage, including oxidative damage, to photoreceptors is disclosed including administering an infective recombinant expression vector that operatively encodes a growth factor under a tissue specific promoter, where the vector is administered intravitreally to the eye of a subject, and upon infection, growth factor expression is substantially restricted to at least one selected tissue in the eye. By the term "tissue specific promoter" herein is meant a regulatory element that selectively controls expression of transcripts in morphologically similar cells, which cells perform one or more select functions.

In a related aspect, the vector includes a glial fibrillary acidic protein (GFAP) promoter. The GFAP promoter sequence is well know in the art (see, e.g., Besnard et al., *J. Biol. Chem.*, 266:18877-18883, 1991; Masood et al., *J. Neurochem.* 61:160-166, 1993; Brenner et al., *J. Neurosci.*, 14:1030-1037, 1994, which papers are incorporated herein by this reference), and vectors containing this promoter are commercially available. The GFAP promoter has been found to have specificity for retinal cells when delivered intravitreally, especially Müller glia.

In another aspect, the method of treating also includes co-administering at least one antiangiogenic agent. In a related aspect, the antiangiogenic agent includes VEGFR-1, NRP-1, angiopoietin 2, TSP-1, TSP-2, angiostatin, endostatin, vasostatin, calreticulin, platelet factor 4, IMP, CDAI, Meth-1, Meth-2, INF-α, INF-β, INF-γ, CXCL10, IL-4, IL-12, IL-18, prothrombin (kringle domain-2) antithrombin III fragment, prolactin, VEGI, SPARC, osteopontin, maspin, canstatin, proliferin-related protein, restin, bevacizumab, carboxyamidotriazol, TNP-470, CM101, suramin, thrombospondin, anti-angiogenic steroids/heparin, cartilage-derived angiogenesis inhibitory factor, an RNA aptamer (e.g., MACUGEN, OSI Pharmaceuticals, Long Island, N.Y.), matrix metalloproteinase inhibitors, 2-methoxyestradiol, Tecogalan, αvβ3 inhibitors, and linomide.

By the term "conditions permissive for the uptake of exogenous nucleic acid" herein is meant experimental conditions which allow an in situ ocular cell to take up, and be transformed with, an exogenous nucleic acid.

The permissive conditions will depend on the form of the exogenous nucleic acid. Thus, for example, when the exogenous nucleic acid is in the form of a viral recombinant expression vector, the permissive conditions are those which allow viral infection of the cell. Similarly, when the exogenous nucleic acid is in the form of a plasmid, the permissive conditions allow the plasmid to enter the cell. Thus, the form of the exogenous nucleic acid and the conditions which are permissive for its uptake are correlated. These conditions are generally well known in the art, and will be employed for in vivo delivery of expression vectors to an ocular cell according to the invention, or for ex vivo transduction of donor cells.

Specific conditions for the uptake of exogenous nucleic acid are well known in the art. They include, but are not limited to, retroviral infection, viral vector infection (e.g., adenoviral, adeno-associated viral (AAV), lentiviral infection), transformation with plasmids, transformation with liposomes containing exogenous nucleic acid, biolistic nucleic acid delivery (i.e. loading the nucleic acid onto gold or other metal particles and shooting or injecting into the cells) and Herpes virus infection. These may all be considered "expression vectors" for the purposes of the invention.

In one embodiment, the vector is an AAV vector. The AAV vector system has been used to express a variety of genes in eukaryotic cells. Hermonat and Muzyczka, *Proc. Natl. Acad. Sci. U.S.A.*, 81:6466-6470, 1984, produced a recombinant AAV (rAAV) viral stock in which the neomycin resistance gene (neo) was substituted for AAV capsid gene and observed rAAV transduction of neomycin resistance into murine and human cell lines. Tratschen et al., *Mol. Cell. Biol.*, 4:2072-2081, 1984, created a rAAV which was found to express the chloramphenicol acetyltransferase (CAT) gene in human cells. Lafare et al., *Virology*, 162:483-486, 1988, observed gene transfer into hematopoietic progenitor cells using an AAV vector. Ohi et al., *J. Cell. Biol.*, 107:304A, 1988, constructed a recombinant AAV genome containing human β-globin cDNA. Wondisford et al., *Mol. Endocrinol.*, 2:32-39, 1988, co-transfected cells with two different recombinant AAV vectors, each encoding a subunit of human thyrotropin, and observed expression of biologically active thyrotropin.

Several rAAV vector systems have been designed. For example, Samulski et al., *J. Virol.*, 61:3096-3101, 1987, constructed an infectious adeno-associated viral genome that contains two XbaI cleavage sites flanking the viral coding domain; these restriction enzyme cleavage sites were created to allow nonviral sequences to be inserted between the cis-acting terminal repeats of AAV. U.S. Pat. No. 4,797,368 relates to AAV vectors contained in a plasmid, capable of being packaged into AAV particles, and functioning as a vector for stable maintenance or expression of a gene or a DNA sequence in eukaryotic cells when under control of AAV transcription promoter. Other AAV vectors and their uses are described in U.S. Pat. No. 5,139,941 and PCT Int'l Patent Appln. WO 94/13788, as well as in Yokoi, et al., *Investigative Ophthalmology and Visual Science*, 48:3324-3328, 2007 (self-complementary AAV vectors).

A number of AAV serotypes are known to have tropism for ocular tissue (see, e.g., Allocca, et al., *Expert Opinion on Biological Therapy*, 12:1279-1294, 2006). Such serotypes are especially preferred for use as expression vectors in the invention, and include AAV2 and AAV5.

Generally, these expression vectors include transcriptional and translational regulatory nucleic acid operably linked to the exogenous nucleic acid. "Operably linked" in this context means that the transcriptional and translational regulatory DNA is positioned relative to the coding sequence of the exogenous protein in such a manner that transcription is initiated. Generally, this will mean that the promoter and transcriptional initiation or start sequences are positioned 5' and/or 3' to the exogenous protein coding region. The transcriptional and translational regulatory nucleic acid will generally be appropriate to the ocular host cell used to express the exogenous protein; for example, transcriptional and translational regulatory nucleic acid sequences from mammalian cells, and particularly humans, are preferably used to express the exogenous protein in mammals and humans. Numerous types of appropriate expression vectors, and suitable regulatory sequences are known in the art.

In general, the transcriptional and translational regulatory sequences may include, but are not limited to, ITRs, TRs, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, for integrating expression vectors, the expression vector contains at least one sequence homologous to the host cell genome, and preferably two homologous sequences which flank the expression construct. The integrating vector may be directed to a specific locus in the host cell (in situ or ex vivo donor cell) by selecting the appropriate homologous sequence for inclusion in the vector. Constructs for integrating vectors are well known in the art.

By "protein useful in the treatment of an ocular disease" herein is meant a protein which is effective to alleviate the symptoms of the ocular disease. The ocular disease may be genetic, or may not have a genetic component. Thus, for example, ocular wounds, allergies, viral infections, ulcerations, and the like, may be treated with useful proteins. For instance, gD is a protein useful in the treatment of herpes simplex virus infections, transforming growth factor β (TGF β) in corneal epithelial wounds; anti-IgE antibody for ocular allergy, and BDNF, GDNF and CNTF for retinal degeneration. Neurotrophin 4 (NT4) and BDNF, as well as fusions and/or mutants of these, may be used for retinal degeneration or to delay or prevent damage after retinovascular disease, or retinal detachment or glaucoma. These neurotrophic factors may also be used to treat optic nerve compression, trauma or demyelination Immunosuppressive proteins may be used to treat graft rejection after corneal transplantation. Vascular endothelial cell growth factor (VEGF) antagonists, such as antibodies or small molecules, may be used to treat neovascular disorders of the retina and vitreous. Basic fibroblast growth factor has been shown to prolong photoreceptor life in rats (Faktorovich et al., Nature 347:83-86 (1990)). However, as noted hereinabove, NT4 is the preferred growth factor for use in the invention, based on superior results obtained using it in models of retinal degeneration described in the Examples.

In embodiment, the protein useful in the treatment of an ocular disease is NT4, where the NT4 is delivered by a vector. In one aspect, the AAV vector is a genetically engineered gene transfer vector derived in whole or in part from adeno-associated virus vector type 2 (AAV2). In a related aspect the AAV vector is AAV/NT4 (referred to in FIG. 1 as "CERE-140"). The CERE-140 construct lacks all viral protein-encoding DNA sequences, but includes the sequence encoding the human neurotrophin-4 protein (NT4) (see, e.g., GENBANK Accession No. NM_006179)). Expression of the NT4 transgene is controlled by the CAG promoter (a fusion of the CMV enhancer with the chicken β-actin gene promoter and a rabbit β-globin gene intron) and human growth hormone.

For delivery to the eye, a "unit dosage" refers generally to the concentration of vector genomes/ml of a pharmaceutically acceptable composition comprised of an expression vector encoding a protein useful in the treatment of an ocular disease; e.g., NT4. Optimally, for delivery of neurotrophin using a viral expression vector, each unit dosage provided according to the invention will comprise a therapeutically effective dosage of the pharmaceutical composition, wherein the composition includes the viral expression vector in a pharmaceutically acceptable fluid and provides from $10^{10}$ up to $10^{15}$ protein expressing vector genomes (vg) per ml of composition. Delivered to the RGC in accord with the invention, $1\times10^{10}$ vg/eye of pharmaceutical composition (AAV2 encoding NT4) produces 33.119±10.517 ng/retina of detectable NT4 protein. Because the retina generally, and the RGC specifically, are relatively small organs, those of ordinary skill in the art should be able to extrapolate dosages used in animal models for practice of the invention to clinical dosages that will be of probable therapeutic benefit in humans.

Actual delivery of the growth factor encoding expression vector according to the invention is by direct introduction of the pharmaceutical composition to the intravitreal space, or by implantation of a donor cell. For the vector-mediated route of administration, injection is a preferred means of delivery. However, especially for non-vector delivery of the exogenous nucleic acid encoding a growth factor into the intravitreal space (e.g., by plasmid), other means of delivery may be suitable, such as microinjection (DePamphilis et al., BioTechnique 6:662-680 (1988)); electroporation (Tonequzzo et al., Molec. Cell. Biol. 6:703-706 (1986), Potter, Anal. Biochem. 174: 361-33 (1988)); chemically mediated transfection such as calcium phosphate transfection (Graham and van der EB, supra, Chen and Okayama, Mol. Cell. Biol. 7:2745-2752 (1987), Chen and Okayama, BioTechnique, 6:632-638 (1988)) and DEAE-dextran mediated transfer (McCutchan and Pagano, J. Natl. Cancer Inst. 41:351-357 (1968)); cationic liposomal mediated transfection (Felgner et al., Proc. Natl. Acad. Sci. USA, 84:7413-7417 (1987), Felgner and Holm, Focus 11:21-25 (1989) and Felgner et al., Proc. West. Pharmacol. Soc. 32:115-121 (1989)) and other methods known in the art.

For delivery by donor cell implantation, the first step is to create donor cells under conditions permissive for the uptake of exogenous nucleic acid therein. The strategy for transferring genes into donor cells in vitro includes the following basic steps: (1) selection of an appropriate exogenous nucleic acid, as described elsewhere above; (2) selection and development of suitable and efficient vectors for gene transfer, as described elsewhere above; (3) preparation of donor cells from primary cultures or from established cell lines; (4) demonstration that the donor implanted cells expressing the new function are viable and can express the transgene products(s) stably and efficiently; (5) demonstration that the transplantation causes no serious deleterious effects; and (6) demonstration of a desired phenotypic effect in the subject.

The choice of donor cells for implantation depends heavily on the nature of the expressed gene, characteristics of the vector and the desired phenotypic result. The donor cells may be actively growing cells such as primary cultures or established cell lines, replicating embryonic ocular cells or replicating adult ocular cells. The cells may also be precursor, progenitor, or stem cells; i.e., cells that are multipotent, in the sense of being capable of developing into a many different cell types, including ocular cells. Ocular cells include retinal neural cells (e.g., rod or cone photoreceptor cells), retinal pigment epithelial (RPE) cells, iris epithelial cells and retinal stem cells (e.g., retinal progenitor cells).

The long-term survival of implanted cells may depend on effects of the viral infection on the cells, on cellular damage produced by the culture conditions, on the mechanics of cell implantation, or the establishment of adequate vascularization, and on the immune response of the host animal to the foreign cells or to the introduced gene product. The mammalian eye has traditionally been considered to be an immunologically privileged organ. It is nonetheless important to minimize the potential for rejection and graft-versus-host reaction induced by the grafted cells by using autologous cells wherever feasible, by the use of vectors that will not produce changes in cell surface antigens other than those associated with the phenotypic correction and possibly by the introduction of the cells during a phase of immune tolerance of the host animal, as in fetal life. Species-matched cells are therefore preferred; e.g., primate cells for delivery to primates, human cells for delivery to humans, and so forth.

"Subject" as used herein includes both humans and other animals and organisms. Thus, the methods are applicable to both human therapy and veterinary applications. For example, the veterinary applications include, but are not limited to, canine, bovine, feline, porcine, equine, and ovine animals, as well as other domesticated animals including reptiles, birds, rabbits, and rodents such as rats, mice, guinea pigs and hamsters. Valuable non-domesticated animals, such as zoo animals, may also be treated. In the preferred embodiment the animal is a mammal, and in the most preferred embodiment the animal is human.

In addition, the methods outlined in the present invention are useful in the creation of ocular disease animal models. That is, mutated copies of genes may be introduced into animals to create models for drug screening and therapy.

The following examples are intended to illustrate but not limit the invention.

EXAMPLES

Figure 2:
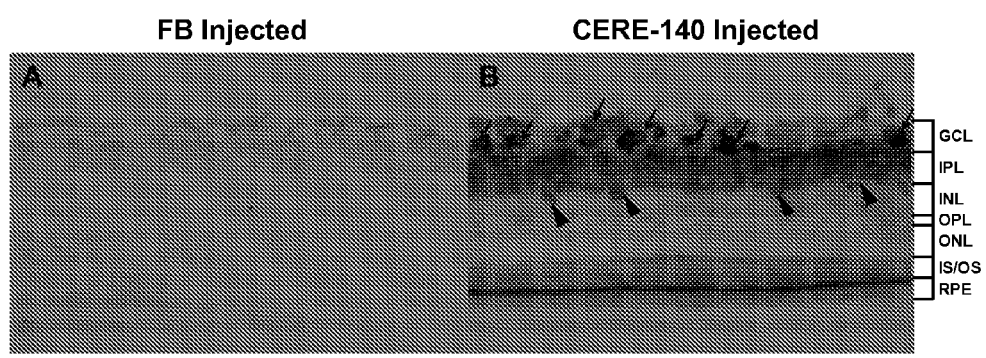
FIG. 2 shows representative images of NT4 immunochemical staining in (A) formulation buffer (FB) control and (B) CERE-140 injected eyes at 4 weeks following intravitreal injection of CERE-140. Red arrows show the expression of NT4 in retinal ganglion, and expression of NT4 throughout the plexiform layer and amacrine cells is identified by the black arrows. GCL=ganglion cell layer; IPL=inner plexifomr layer; INL=inner nuclear layer; OPL=outer plexiform layer; ONL=outer nuclear layer; IS=inner segment; OS=outer segment; RPE=retinal pigmented epithelium.

1. NT4 Expression in the Retina Following AAV/NT4 Intravitreal Administration AAV/NT4 mediated expression and subsequent secretion of NT4 from transduced retinal cells was confirmed by immunohistochemistry (FIG. 2). Following intravitreal injection, NT4 was distributed primarily throughout the innermost retinal ganglion cell (RGC) layer in the retina. NT4-positive inner nuclear layer cells (amacrine, bipolar, and/or horizontal cells) and occasional Müller glia cells are also detected in the retina following intravitreal injection of AAV/NT4. Slight NT4 labeling is also seen in the photoreceptor segments following intravitreal injection of AAV/NT4. In addition, NT4 protein is also anterogradely transported from RGCs to retino-recipient areas of the brain, primarily the lateral geniculate nucleus and superior colliculus regions of the brain via the visual pathway.

The amount of NT4 in isolated retina at 4 weeks following intravitreal administration of AAV/NT4 ($1 \times 10^{10}$ vg/eye) has also been quantified by ELISA. The concentration of NT4 is $1.015 \pm 0.259$ ng/mg tissue (mean±SEM) or $33.119 \pm 10.517$ ng/retina. Control retinas from naïve and FB injected eyes are all below the lower limit of quantitation (LLOQ) for the assay (0.032 ng/ml).

2. Efficacy of Intravitreal AAV/NT4 in Animal Models of Photoreceptor Degeneration The efficacy of AAV/NT4 has been demonstrated in several experimental rat models of photoreceptor degeneration, including the P23H line 1 (P23H-1) and S334 line 4 (S334-4) transgenic rat models of retinitis pigmentosa (RP), as well as the constant light damage model of photoxic retinal degeneration (in wild type albino Sprague Dawley rats). Table 1 shows the rate of photoreceptor degeneration (and hence severity of the model), which routes of AAV/NT4 were tested, and the experimental measures performed for these three models.

TABLE 1

Rat models used to test the efficacy of intraocular AAV/NT4, and corresponding outcome measures.

| | | | Experimental Outcome Measures | |
|---|---|---|---|---|
| Rat Model | Mutation | Degeneration Rate | Subretinal CERE-140 | Intravitreal CERE-140 |
| P23H Line 1 | Rhodopsin: single amino acid substitution at codon 23* | Moderate | ERG ONL Thickness | ERG ONL Thickness |
| S344 Line 4 | Rhodopsin: C-terminal truncation of last 15 amino acids | Moderate | ERG ONL Thickness | ERG ONL Thickness |
| Constant Light Damage | N/A | Very Rapid | ONL Thickness | ERG ONL Thickness |

*Most common mutation in RP.
N/A = not applicable.
ERG = electroretinogram;
ONL = outer nuclear layer (consisting of the photoreceptor nuclei).

Two primary consequences of photoreceptor degeneration in these 3 models are 1) a decrease in the electrophysiological response of retinal neurons in response to light flash stimulation, as measured by electroretinogram (ERG), and 2) a decrease in the number of photoreceptor cells, and therefore, in the outer nuclear layer (ONL) thickness, where the photoreceptor cell bodies reside in the retina. Whereas the ONL thickness measurements provide a quantitative anatomical index of the amount of photoreceptor degeneration, ERG measurements assess the function of the retina.

The three principal components of ERG measurements are the scotopic b-wave, the scotopic a-wave, and the photopic b-wave (see Table 2).

TABLE 2

ERG signals and their cellular and functional measures.

| ERG signal | Associated cell type(s) | Functional measure |
|---|---|---|
| Scotopic b-wave | Inner nuclear layer cells | Global functioning, including downstream elements |
| Scotopic a-wave | Rod photoreceptors | Peripheral, low light, monochromatic vision |
| Photopic b-wave | Cone photoreceptors | Central, bright light, color vision |

The scotopic b-wave primarily reflects the health of the inner retinal cells, including bipolar and Müller cells, and therefore, represents a measure of the global functioning of the retina. The scotopic a-wave reflects the functional response primarily of the rod photoreceptors, the cell type predominantly responsible for peripheral monochromatic vision in low light. The photopic b-wave reflects the functional response primarily of cone photoreceptors, the cell type predominantly responsible for central color vision in bright light.

For efficacy experiments involving the P23H-1 and S334-4 lines, the transgenic rats were injected at P11-12 (i.e., 11 to 12 days, post-natal). For the constant light damage model, rats were injected approximately 4 weeks before exposure to the constant light. In all cases, rats were injected unilaterally intravitreally with $2.4 \times 10^{10}$ AAV/NT4 vg/eye in a total volume of 2 μl. The contralateral eyes were injected with 2 μl of formulation buffer (FB) for within animal controls. Electroretinogram measurements were taken prior to sacrifice at P60-

64 for the P23H-1 and S334-4 rats or after 7 days of constant light exposure to assess the physiological health of the retina in AAV/NT4 injected eyes as compared to the contralateral control eyes. After sacrifice, eyes were processed for histology to measure outer nuclear layer (ONL) thickness and qualitatively evaluate retinal structure.

Figure 3:
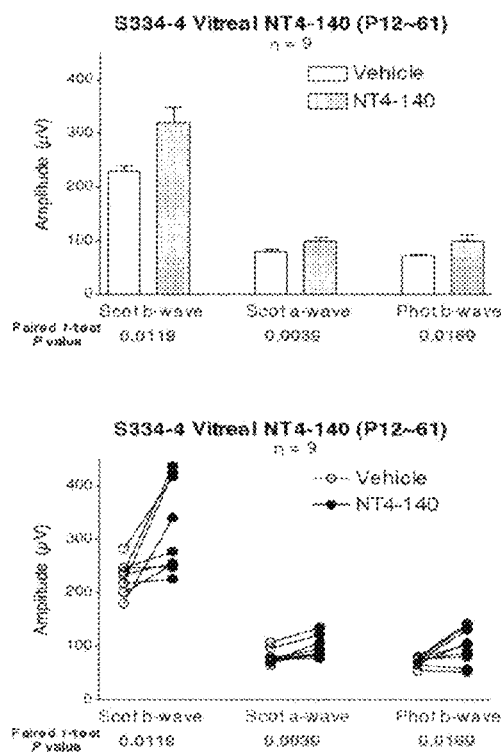
FIG. 3 shows ERG results following intravitreal injections of CERE-140 (NT4-140) in P23H-1 (left panels) and S334-4 (right panels) transgenic rat models of RP. Histograms of the mean ERG amplitudes are presented in the top panels. Error bars represent standard errors of the mean (SEM). The individual data points for each rat are plotted in the two lower panels with data from contralateral eyes connected by lines.

ERG Data. Following intravitreal administration of AAV/NT4, all b-wave and a-wave ERG responses were significantly improved in both P23H-1 and S334-4 models compared to formulation buffer injected or uninjected contralateral control eyes (FIG. 3). The increases seen in scotopic b-wave, scotopic a-wave, and photopic b-wave amplitudes were highly significant in both models (p values: 0.0002 for scotopic b-wave, 0.0004 for scotopic a-wave, and <0.0001 for photopic b-wave amplitudes in the P23H-1 model; 0.0119 for scotopic b-wave, 0.0039 for scotopic a-wave, and 0.0169 for photopic b-wave amplitudes in the S334-4 model: FIG. 3). These results indicate that intravitreal AAV/NT4 can prevent or reduce the functional deficits associated with the photoreceptor degeneration in these models of RP, and can specifically protect or restore the health of rods, cones, and other downstream inner retinal cells, such as bipolar cells and Müller glia cells. Furthermore, these results suggest that the intravitreal route of administration is more efficacious than the subretinal route at providing functional protection from photoreceptor degeneration, specifically for the rod photoreceptor population.

Figure 4:
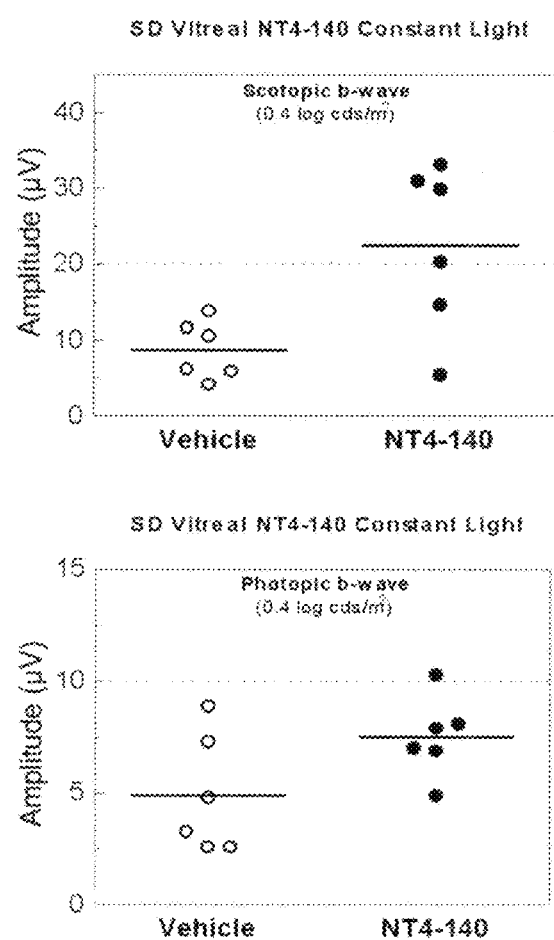
FIG. 4 shows ERG results following intravitreal CERE-140 (NT4-140) in the constant light damage model of photoreceptor degeneration. Mean amplitudes for scotopic b-wave (left panel) and photopic b-wave (right panel) responses are designated by the solid line within the individual data point clusters.

Intravitreal AAV/NT4 also had a positive effect on both scotopic b-wave and photopic b-wave ERG response in the constant light damage model (FIG. 4). Although there was considerable variability between eyes, the mean scotopic and photopic b-wave amplitudes in both models were greater that in control eyes following intravitreal AAV/NT4 injection. Scotopic a-wave amplitudes were absent from these measurements in all eyes due to the severity of the degeneration. Therefore, there was a trend for AAV/NT4 to protect retinal function (particularly that of the inner nuclear layer cells and cones), however, rod functionality was still impaired in this severe model of degeneration.

Following intravitreal injections, histological analyses consistently revealed a significant increase in outer nuclear (ONL) thickness throughout the retina in AAV/NT4 injected eyes compared to FB injected contralateral control eyes in the P23H-1 and constant light damage models, with a meaningful increase that, however, did not reach statistical significance in the S334-4 model. For each model, representative images of retinal cross-sections are shown, as well as a "spider graph" of the mean ONL thickness measurements taken from region-matched areas across the retina for AAV/NT4 injected and control eyes.

Figure 5:
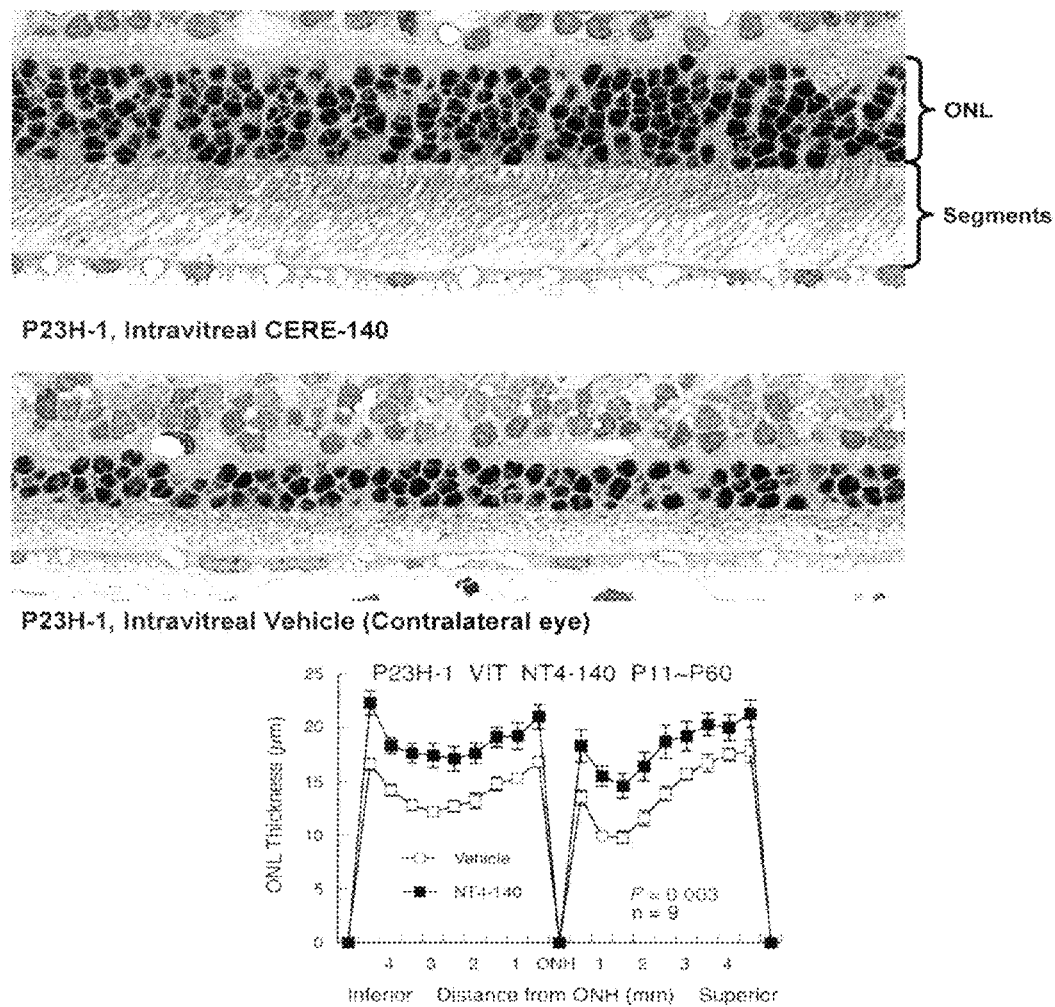
FIG. 5 shows ONL thickness following intravitreal CERE-140 injection in the P23H-1 transgenic rat model of RP. Representative retinal cross-sections in the superior aspect of the retina of a CERE-140 (NT4-140; upper photomicrograph) injected eye compared to the contralateral vehicle injected control eye (lower photomicrograph) are shown. The "spider graph" beneath the photomicrographs illustrates the difference in ONL thickness at multiple matched sites across the retina in the midline plane. ONH=optic nerve head.

For the P23H-1 transgenic mouse model, FIG. 5 shows the ONL (identified by the layer of darkly stained cells) in AAV/NT4 injected eyes appears thicker with a greater number of photoreceptor cell body rows. In addition, unlike the control eyes, AAV/NT4 injected eyes have robust outer and inner photoreceptor segments with proper morphology and alignment. The "spider graph" indicates that the neuroprotective effects of intravitreal AAV/NT4 were manifested throughout the retina and were not confined to a focal region. Furthermore, the increase in ONL thickness in AAV/NT4 injected eyes was highly significant ($p=0.003$).

Figure 6:
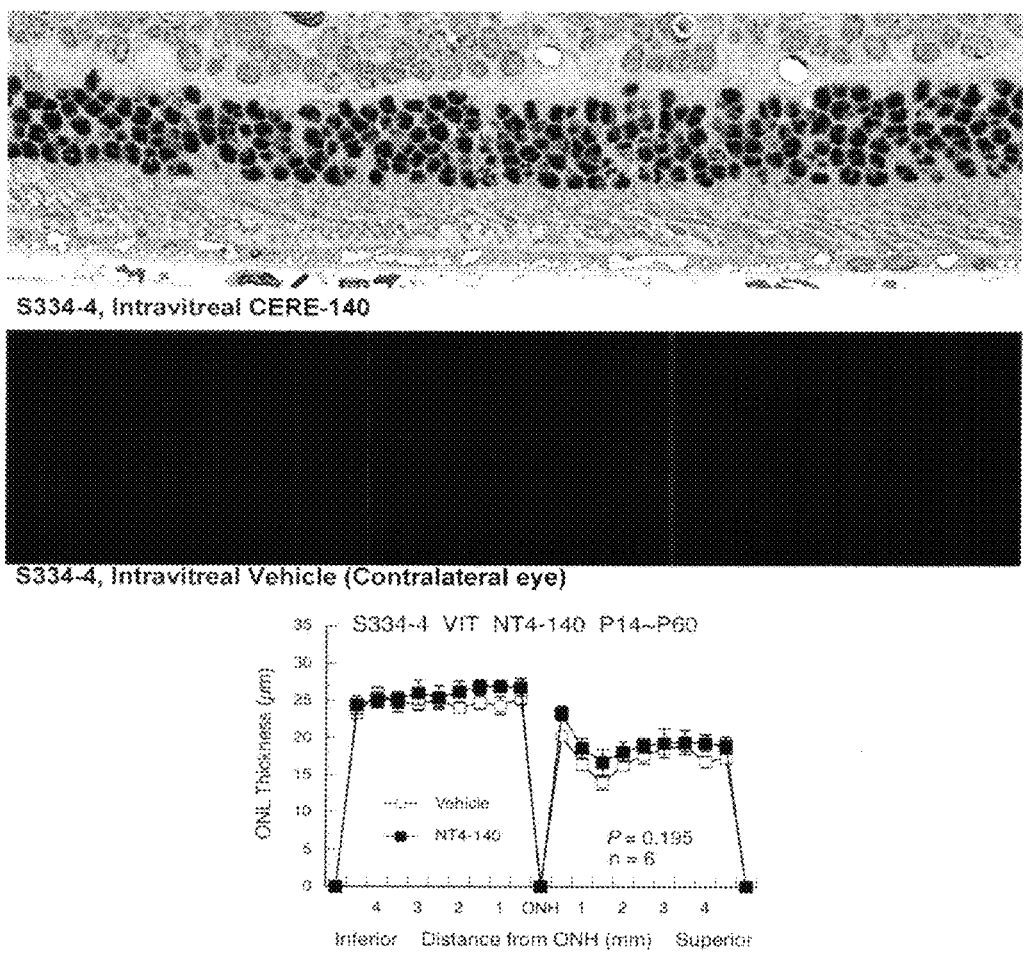
FIG. 6 shows ONL thickness following intravitreal CERE-140 injection in the S334-4 transgenic rat model of RP. Representative retinal cross-sections in the superior aspect of the retina of a CERE-140 (NT4-140; upper photomicrograph) injected eye compared to the contralateral vehicle injected control eye (lower micrograph) are shown. The "spider graph" beneath the photomicrographs illustrates the difference in ONL thickness at multiple matched sites across the retina in the midline plane. ONH=optic nerve head.

For the S334-4 transgenic mouse model, FIG. 6 shows that the photoreceptor outer and inner segments appear healthier with proper morphology and alignment in the AAV/NT4 injected eyes compared to the controls. The "spider graph" reveals a trend for increased ONL thickness, but this effect was not statistically significant ($p=0.195$).

Figure 7:
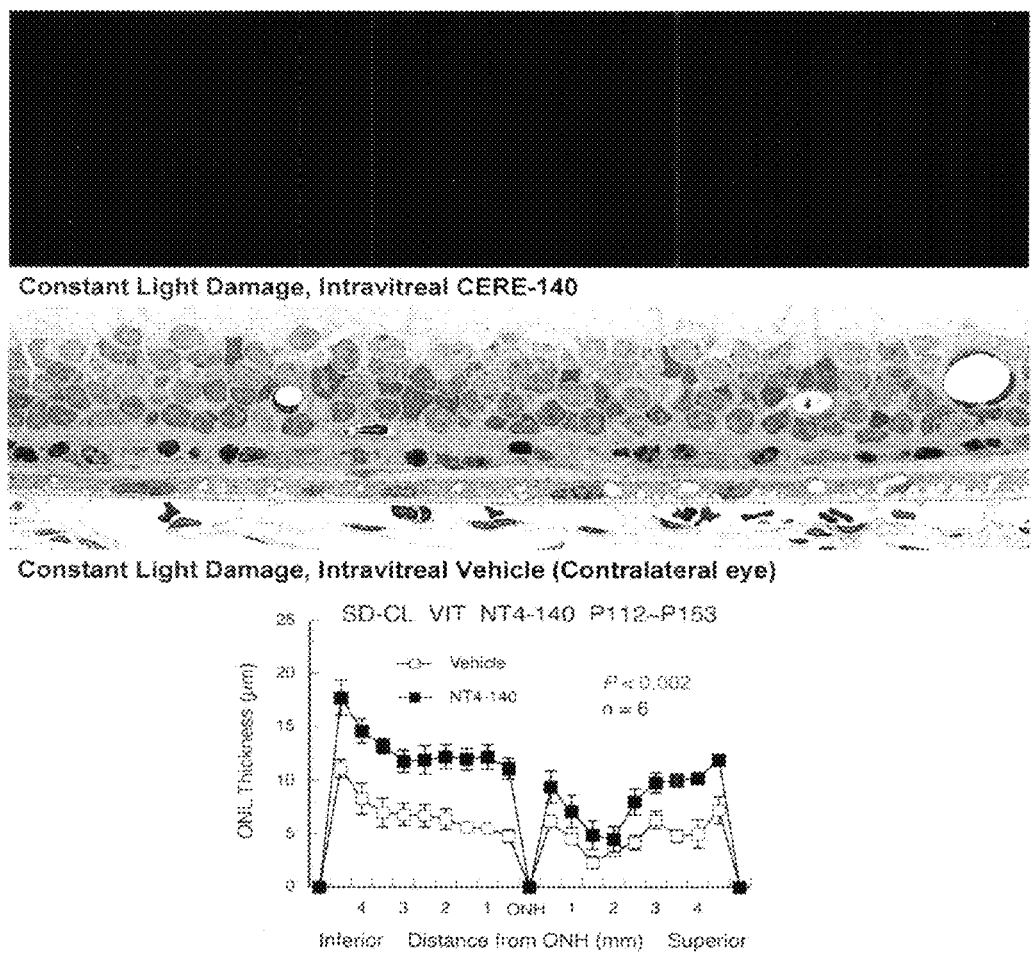
FIG. 7 shows ONL thickness following intravitreal CERE-140 injection in the constant light damage model of retinal degeneration. Representative retinal cross-sections in the superior aspect of the retina of a CERE-140 (NT4-140; upper photomicrograph) injected eye compared to the contralateral vehicle injected control eye (lower photomicrograph) are shown. The "spider graph" beneath the photomicrographs illustrates the difference in ONL thickness at multiple matched sites across the retina in the midline plane. ONH=optic nerve head.

For the constant light damage model, FIG. 7 shows that although both retinas are substantially degenerated, increased ONL thickness in the AAV/NT4 injected eye is clearly visible. Note that the photoreceptors in the control vehicle injected eyes are nearly completely absent at this stage in the model, revealing the severity of the model. The "spider graph" indicates that the neuroprotective effects of intravitreal AAV/NT4 were manifested throughout the retina and were not confined to a focal region. Furthermore, the increase in ONL thickness in the AAV/NT4 injected eyes was highly significant ($p<0.002$), even in this severe and rapid model of photoreceptor degeneration.

3. Comparison of Intravitreal AAV/NT4 Efficacy Results to Those Obtained with Subretinal Injections Intravitreal AAV/NT4 injection resulted in morphological improvements on photoreceptor ONL thickness in all 3 rat models tested, with significant increases in the P23H-1 and constant light damage models. There was a trend for increased ONL thickness in the S334-4 model, with a subset of rats clearly responding to the treatment. In addition, intravitreal AAV/NT4 resulted in a significant gain in ERG scotopic a-wave; since the scotopic a-wave reflects the functional health of rod photoreceptors, the most abundant photoreceptor cell type in the retina, AAV/NT4 presumably exerts a neuroprotective effect on the rod photoreceptor population when administered intravitreally. Also, ERG results revealed significant increases in scotopic and photopic b-wave amplitudes for intravitreal AAV/NT4 administration, suggesting that AAV/NT4 mediated delivery of NT4 to the retina may also benefit the health of cones and inner retinal cells.

Subretinal injection of AAV/NT4 results in NT4 protein expression primarily in photoreceptor cells themselves, with some additional expression in retinal pigmented epithelium (RPE). In contrast to the intravitreal results, results from subretinally administered AAV/NT4 showed no change in photoreceptor cells in any of these 3 models. ONL thickness measurements revealed no difference between AAV/NT4 injected and FB injected (or uninjected) eyes when administered subretinally in P23H-1 and S334-4 transgenic models or the constant light damage model. Given the lack of significant photoreceptor sparing following subretinal AAV/NT4 injection, it is not surprising that there was no significant improvement in scotopic a-wave ERG response in these models either, since the scotopic a-wave represents the functional status of rods—the most abundant photoreceptor cell type in the ONL. For both P23H-1 and S334-4 lines, ERG measurements revealed a significant increase in the scotopic b-waves and photopic b-waves of AAV/NT4 injected eyes compared to the contralateral FB injected controls (paired t-tests p values: 0.0057 for scotopic b-wave, 0.0009 for photopic b-wave amplitudes in the P23H-1 model; 0.0027 for scotopic b-wave, 0.0019 for photopic b-wave amplitudes in the S334-4 model) (FIG. 4). However, the sizes of these positive changes with subretinal AAV/NT4 injection are much less than those observed for intravitreal AAV/NT4 in the same model. Therefore, histological and functional analyses suggest that the intravitreal route of AAV/NT4 administration is more efficacious at protection of photoreceptor degeneration than the subretinal route.

Very few photoreceptors are transduced following intravitreal AAV/NT4 injection. However, since subretinal injections target the photoreceptors directly but do not cause photoreceptor cell loss, NT4 expression in photoreceptors does not appear to be necessary for widespread neuroprotection.

Therefore, another cell type such as a Müller cell may provide the trophic support necessary to prevent photoreceptor cell death or loss of function when stimulated by NT4. In either case, intravitreal administration appears to offer a greater amount of histological and functional protection, particularly for rod photoreceptors, than does subretinal administration.

4. NTN Expression in the Retina Following AAV/NTN Intravitreal Administration CERE-120 is a genetically engineered gene transfer vector derived from adeno-associated virus vector type 2 (AAV2). CERE-120 is identical in structure and sequence to CERE-140, except the sequence encoding the human NT4 protein in CERE-140 is replaced with the sequence encoding the mature human neurturin (NTN) protein fused to the human β-nerve growth factor (βNGF) pre/pro sequence in CERE-120.

Figure 8:
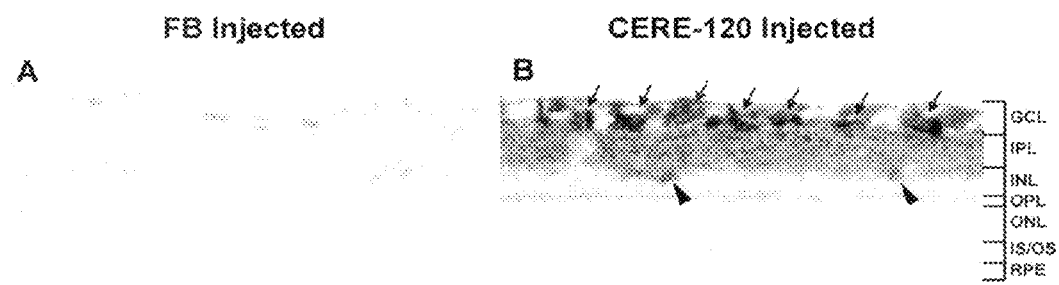
FIG. 8 shows photomicrograph images of neurturin (NTN) immunohistological staining in (A) formulation buffer (FB) control and (B) AAV/NTN (CERE-120 construct) injected eyes at 4 weeks following intravitreal injection. GLC=ganglion cell layer; IPL=inner plexiform layer; INL=inner nuclear layer; OPL=outer plexiform layer; ONL=outer nuclear layer; IS=inner segment; OS=outer segment; RPE=retinal pigmented epithelium.

AAV/NTN mediated expression and subsequent secretion of NTN from transduced retinal cells has been confirmed by immunohistochemistry (see FIG. 8). Following intravitreal injection, NTN is distributed primarily through the innermost retinal ganglion cell (RGC) layer in the retina. NTN-positive inner nuclear layer cells (amacrine, bipolar, and/or horizontal cells) and occasional Müller glia cells are also detected in the retina following intravitreal injection of AAV/NTN. Slight NTN labeling is also seen in the photoreceptor segments following intravitreal injection of AAV/NTN. The NTN transgene expression pattern observed following intravitreal AAV/NTN is virtually identical to that seen with NT4 following intravitreal CERE-140 (AAV/NT4) administration.

5. Efficacy of Intravitreal AAV/NTN in Animal Models of Photoreceptor Degeneration The efficacy of AAV/NTN was investigated in several experimental rat models of photoreceptor degeneration, including the P23H line 1 (P23H-1) and S334 line 4 (S334-4) transgenic rat models of retinitis pigmentosa (RP), as well as the constant light damage model of phototoxic retinal degeneration (in wild type albino Sprague Dawley rats). These are the same models in which the effects of intravitreal AAV/NT4 were tested, and the outcome measures examined for both the CERE-140 and AAV/NTN vectors were also the same.

For efficacy experiments involving the P23H-1 and S334-4 lines, the transgenic rats were injected at P12 or P15 (i.e., 12 or 15 days post-natal), respectively. For the constant light damage model, wild type rats were injected approximately 4 weeks before exposure to the constant light. In all cases, rats were injected unilaterally intravitreally with $2.4 \times 10^{10}$ AAV/NTN vg/eye in a total volume of 2 µl. The contralateral eyes were injected with 2 µl of formulation buffer (FB) for within animal controls. Electroretinogram measurements were taken prior to sacrifice at P60 for the P23H-1 rats, P65 for the S334-4 rats, or after day 7 of constant light exposure in the wild type rats, to assess the physiological health of the retina in AAV/NTN injected eyes as compared to the contralateral control eyes. After sacrifice, eyes were processed for histology to measure outer nuclear layer (ONL) thickness and qualitatively evaluate retinal structure.

Figure 9:
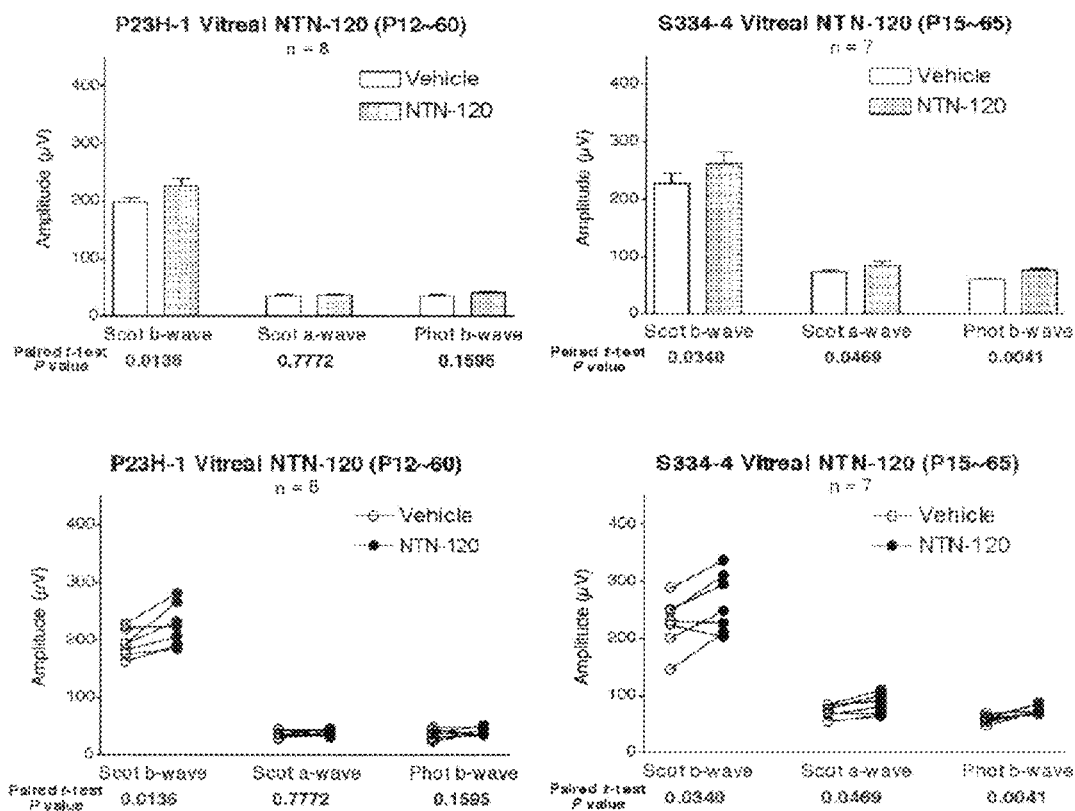
FIG. 9 shows histograms for ERG results following intravitreal injections of CERE-120 (NTN-120) in P23H-1 (left panels) and S334-4 (right panels) transgenic rat models of RP. Histograms of the mean ERG amplitudes are presented in the top panels. Error bars represent standard errors of the mean (SEM). The individual data points for each rat are plotted in the two lower panels with data for contralateral eyes connected by lines.

ERG Data. Intravitreal administration of AAV/NTN produced modest functional benefits in both P23H-1 and S334-4 models compared to FB injected or uninjected contralateral control eyes (FIG. 9). In the P23H-1 model, AAV/NTN mediated NTN delivery resulted in a significantly increased scotopic b-wave only (p=0.0136). In the 5334-4 model, significant increases were seen in all three waves (p values: 0.0340 for scotopic b-wave, 0.0469 for scoptopic a-wave, and 0.0041 for photopic b-wave amplitudes). In comparison, the same dose of AAV/NT4 (to deliver NT4) resulted in significant increases in all 3 waves in both models, and both the magnitude and the significance of these increases were much greater with AAV/NT4 than with AAV/NTN (compare FIGS. 3 and 4 with FIG. 9).

Figure 10:
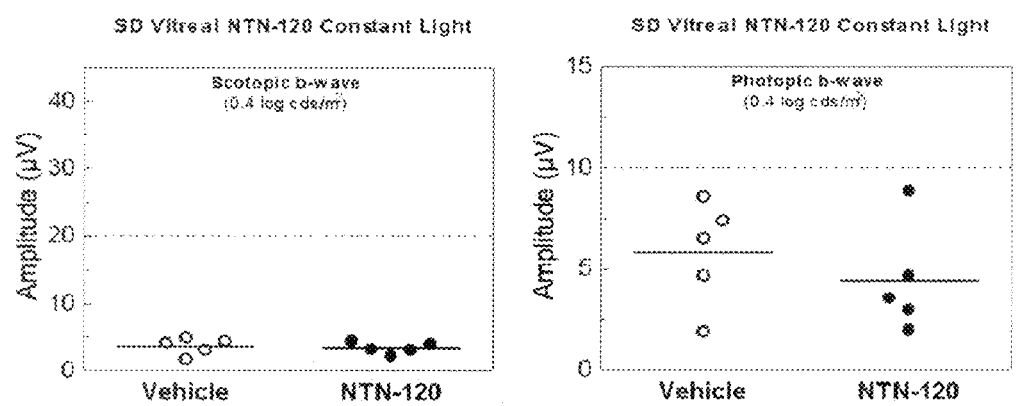
FIG. 10 shows histograms for ERG results following intravitreal CERE-120 (NTN-120) in the constant light damage model of photoreceptor degeneration. Mean amplitudes for scotopic b-wave (left panel) and photopic b-wave (right panel) responses are designated by the solid line within the individual data point clusters.

No improvements were seen with intravitreal AAV/NTN in any of the 3 ERG waves in the constant light model (FIG. 10). Scotopic a-wave amplitudes were absent from these measurements in all eyes due to the severity of the degeneration. In comparison, intravitreal AAV/NT4 resulted in mean improvements of both scotopic b-wave and photopic b-wave ERG responses, however, due to variability, these increases did not reach statistical significance. Nevertheless, there was a trend for AAV/NT4 to protect retinal function (particularly that of inner nuclear layer cells and cones), whereas AAV/NTN was not efficacious in this severe model of degeneration.

Histological Data. Histological analyses revealed that intravitreal AAV/NTN injection has absolutely no effect on outer nuclear layer (ONL) thickness throughout the retina compared to FB-injected contralateral control eyes in the P23H-1 and S334-4 transgenic rat models or in the constant light damage model of RP. In comparison, significantly increased ONL thicknesses were seen throughout the retina following intravitreal AAV/NT4 in the P23H-1 and constant light damage models, with a trend for increased ONL thickness in the S334-4 model (see FIGS. 5, 6, and 7).

6. Intravitreal CERE-140 in rcd3 Dog Model of Photoreceptor Degeneration

The rcd3 dog model of photoreceptor degeneration. rcd3 dog is a strain of Cardigan Welsh corgi dog that carries a mutation in the PDE6A gene. This gene encodes the alpha subunit of cyclic-GMP-specific phosphodiesterase 6A, a protein expressed in the outer segments of rod photoreceptors that regulates membrane current and thus participates in the transmission and amplification of the visual signal. Mutations in PDE6A can lead to a phenotype of progressive retinal atrophy known as rod-cone dysplasia, characterized by the initial loss of rod photoreceptors and the subsequent loss of cone photoreceptors.

The rod-cone dysplasia in the rcd3 dog is early onset and extremely rapid. A similar pattern of photoreceptor degeneration occurs in retinitis pigmentosa (RP) and several other blinding diseases, albeit at a slower rate of progression. Furthermore, PDE6A mutations specifically account for a small percentage of RP cases. Therefore, the rcd3 dog is a relevant model to test potential therapies for RP and other diseases of photoreceptor degeneration.

Efficacy of intravitreal CERE-140 in the rcd3 dog model. Studies in rats have demonstrated that maximal transgene expression of AAV2-based vectors in the retina occurs at approximately 4 weeks post intravitreal injection. Therefore, rcd3 dogs were dosed with CERE-140 at early time points to assure adequate expression of NT4 relative to the onset of pathology. A total of 8 dogs each received a single intravitreal injection of CERE-140 in the right eye. Five dogs were injected with 15 µL of CERE-140 (total dose: $3.8 \times 10^{11}$ vg) on postnatal Day 4, and 3 dogs were injected with 20 µL of CERE-140 (total dose: $5.0 \times 10^{11}$ vg) on Day 9 (n=1) or Day 12 (n=2). The contralateral left eye was injected intravitreally with an equal volume of Formulation Buffer to serve as a within-animal control.

Electroretinogram (ERG) measurements were taken at approximately 7 weeks of age to assess cone function in response to light flashes. Since rods are not functional in rcd3 mutant dogs from a very early age, the functional recovery of the rods was not expected in this model. Therefore, only those ERG measurements that reflect the health of cone photoreceptors specifically were analyzed. The two relevant ERG measurements of cone function are the photopic a-wave, a component of the ERG signal resulting from a single flash of bright light under normal lighting conditions, and the cone flicker response, the electrical signal resulting from a high frequency (approximately 30 Hz) flicker of bright white light that selectively stimulates cones.

Figure 11:
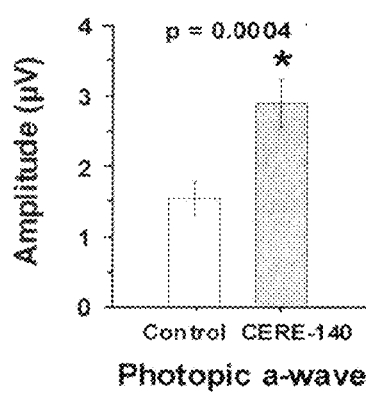
FIG. 11 shows ERG results following intravitreal CERE-140 (NT4-140) in the rcd3 dog model of photoreceptor degeneration. Mean values (top panels) and individual values (bottom panels) for photopic a-wave and flicker ERG amplitudes. Error bars represent standard errors of the mean (SEM). The individual data points for each animal are plotted in the two lower panels with data for contralateral eyes connected by lines. There was a significant increase in the photopic a-wave (p=0.004) and cone flicker amplitudes (p=0.01) in CERE-140 injected eyes compared to contralateral formulation buffer injected control eyes.
Figure 11:
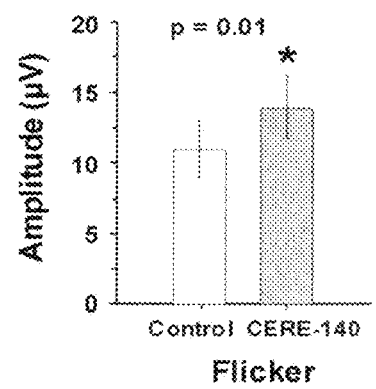
Figure 11:
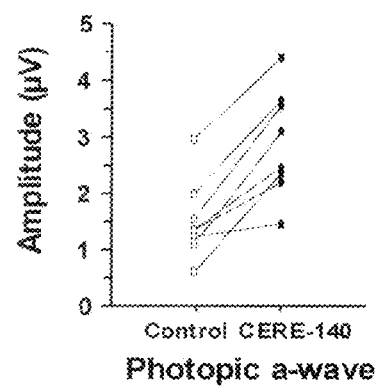
Figure 11:
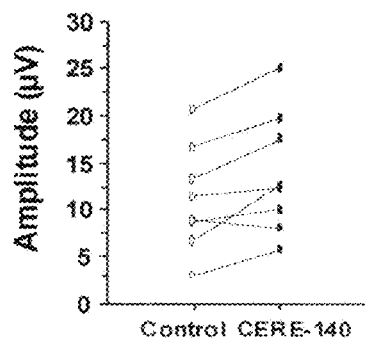

ERG Results. Results of the ERG data acquired at 7 weeks are presented in FIG. 11. Compared to formulation buffer injected control eyes, significant increases were seen in both photopic a-wave and cone flicker responses. The significant increases in ERG amplitudes of the photopic a-wave and flicker responses observed in CERE-140 injected eyes indicates that CERE-140 protected cone function in the rcd3 model of photoreceptor degeneration, preserving the electrophysiological activity of cone photoreceptors. In humans, such treatment should prevent the loss of central, high acuity, color vision.

7. Combination Therapy of Abnormal Retinal Neovascularization in vldlr$^{-/-}$ Mice and Tissue Specificity of the GFAP Promoter Mice deficient for VLDLR (vldlr$^{-/-}$) appear outwardly normal, are viable and fertile (Frykman et al., *Proc. Natl. Acad. Sci. USA*, 92:8453-8457, 1995), but exhibit abnormalities in the retinal vasculature (Heckenlively et al., *Retina*, 23:518-522, 2003; Li et al., *Arch. Ophthalmol.*, 125:793-803, 2007). Systematic evaluation of neonatal vldlr$^{-/-}$ mice revealed normal development of retinal vessels through the first postnatal week. During the second postnatal week, vldlr$^{-/-}$ retinas exhibited transient hyperproliferation of the superficial vascular plexus and associated astrocytes, particularly in newly vascularized regions near the retinal periphery. This associated astrocytosis is consistent with previous studies demonstrating a direct correlation between vessels and astrocytes in the superficial retina (Dorrell et al., *Invest. Ophthalmol. Vis. Sci.*, 43:3500-3510, 2002; Stone and Dreher, *J. Comp. Neurol.*, 255:35-49, 1987; Fruttiger et al., *Neuron*, 17:1117-1131, 1996). By the third postnatal week, vessel and astrocyte density in the superficial plexus receded to normal levels.

By the fifth postnatal week, the normal RPE monolayer was disrupted around subretinal vascular lesions and multiple layers of RPE cells enveloped the neovascular complexes in vldlr$^{-/-}$ retinas. The accumulated abnormalities over a 5 week period lead to focal distortion and scarring of the retina, and are associated with focal loss of photoreceptor inner (PIS) and outer (POS) segments, demonstrated by abnormal retinal morphology and an absence of red/green (rd/gr) opsin staining in regions with subretinal neovascularization. Photoreceptor degeneration was also observed. Neural abnormalities never preceded appearance of intra- and subretinal neovascularization. At post-natal day 12 (P12), just prior to the onset of abnormal neovascularization, all retinal layers were intact and identical to age-matched wild-type C57BL6/J (WT) controls when evaluated by electron and confocal microscopy. Thus, neural abnormalities in vldlr$^{-/-}$ mouse retinas appear to be the result, rather than a cause, of neovascularization.

Although a striking reduction in the formation of subretinal neovascularization can be obtained using anti-angiogenic therapy (e.g., with MACUGEN, an integrin αbβ3 and αbβ5 antagonist together with T2-TrpRS, a fragment of tryptophan tRNA synthetase with anti-angiogenic activity), the effect was only transient; subretinal neovascularization returned in treated animals within 2-3 weeks following treatment. This is similar to clinical observations which report beneficial effects of anti-angiogenics, but with effects that are often only partial, and generally involve chronic therapy. Thus, additional strategies for protecting retinal vision in ocular vascular diseases are still required (Bradley and Robinson Angiogenesis (2007) 10:141-148). Further analysis was performed using neurotrophic factors specifically delivered to sites of retinal neovascularization, and therefore active sites of retinal degeneration, as agents to protect retinal neuronal function in eyes with vascular disease.

0.5 μL solutions of adeno-associated virus particles containing AAV-CAG-GFP (CAG promoter driven GFP expression), AAV-GFAP-GFP (GFAP promoter driven GFP expression), or AAV-GFAP-NT4 (GFAP promoter driven neurotrophin-4 expression), titers ~1e13 vg/mL, were injected intravitreally into 2 week old vldlr$^{-/-}$ mouse eyes. Viral transfection was assessed by analyzing GFP expression at 1 and 2 months following injection. Effects on the neurodegenerative phenotype of vldlr$^{-/-}$ mice were assessed 3 months post-injection.

GFAP activation in Müller cells occurs specifically around subretinal neovascularization in the vldlr$^{-/-}$ mouse retina. Intravitreal injection of a GFP vector (AAV-GFAP-GFP) demonstrated that expression was limited to the inner retina in control, WT mice (FIG. 12A). However, GFP expression was observed throughout the inner and outer retinas of vldlr$^{-/-}$ mice, specifically expressed by the activated Müller cells adjacent to subretinal neovascularization (FIG. 12C-D). In contrast, a control vector with a ubiquitous CAG-driven promoter (AAV-CAG-GFP) demonstrated non-specific expression of GFP by all cells of the inner retina, but minimal expression in the outer retina (FIG. 12B). By targeting the activated Müller glia using the AAV viral vector with a GFAP promoter, specific deliver of vector products to the outer retina in areas directly adjacent to subretinal neovascularization was obtained.

Neurotrophin-4 (NT-4) has been shown to protect neurons in several models of neuronal degeneration including retinal degeneration (Lykissas et al., *Curr. Neurovasc. Res.*, 4:143-151, 2007; Harada et al., *Invest. Ophthalmol. Vis. Sci.*, 46:669-673, 2005). Similar to the GFP vectors, AAV-2 vectors with GFAP driven expression of NT-4 (AAV-GFAP-NT4) resulted in NT-4 production in activated Müller cells specifically adjacent to intraretinal neovascularization (FIG. 12E). This resulted in extensive accumulation of NT-4 at the outer and inner segments of photoreceptors near areas of subretinal neovascularization throughout the central two-thirds of the retina (FIG. 12F).

Figure 12H:
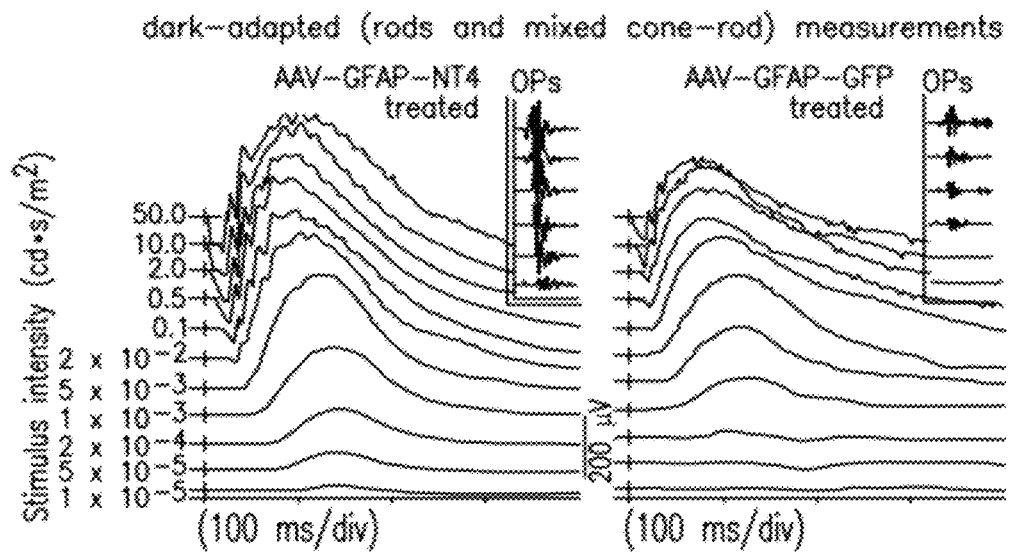
FIG. 12 demonstrates that targeted delivery of NT4 to sites of subretinal neovascularization protects vldlr$^{-/-}$ retinas from neuronal degeneration. (A-D) Adeno-associated virus 2 (AAV2) plasmids under the control of the GFAP promoter selectively result in gene product expression in activated Müller cells surrounding areas of subretinal neovascularization. All virus preparations were injected at P14. (A) WT retinas infected with AAV-GFAP-GFP. (B) WT retinas infected with control CAG-driven promoter vector (AAV-CAG-GFP). (C-D) Expression of GFP in Müller cells 2 weeks following injection (P28, C) and 1 month following injection (P45, D). (E-F) shows the localization of NT4 gene product near subretinal areas surrounding abnormal neovascularization. (G) Provides quantitative RT-PCR analysis of opsin-1 and rhodopsin mRNA in areas surrounding subretinal neovascularization. (H-I) Provides ERG analysis of AAV-GFAP-NT4 treatment on retinal function. (J) Provides quantification analysis of ERG measurements comparing 3-4 month old WT mice, 3-4 month old untreated vldlr$^{-/-}$ mice, 4 month old AAV-GFAP-GFP control treated vldlr$^{-/-}$ mice, and 4 month old AAV-GFAP-NT4 treated vldlr$^{-/-}$ mice. Bold p-values indicate statistically significant measurements between contralaterally treated AAV-GFAP-NT4 and AAV-GFAP-GFP eyes.
Figure 12I:
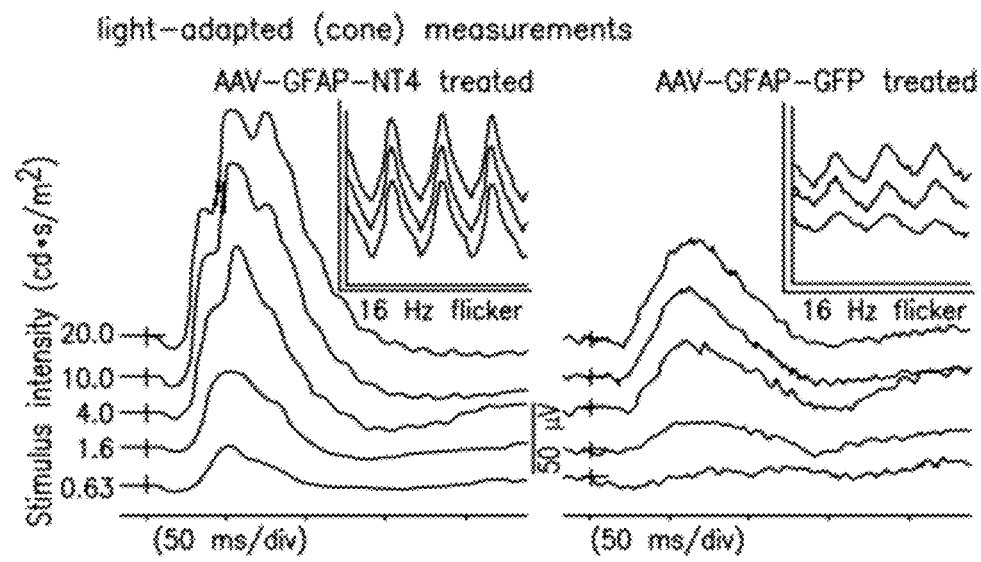

Use of the AAV-GFAP-NT4 vector protected the retina from neuronal degeneration as observed by the normalization of opsin and rhodopsin mRNA expression (FIG. 11G), and protected the vldlr$^{-/-}$ retinas from the characteristic loss of visual function as observed by ERG analysis (FIG. 12H-J). This protection, provided by the selective delivery of a neurotrophic factor to retinal areas with subretinal neovascularization, is strongly suggestive of a direct correlation between abnormal neovascularization and neuronal degeneration in the retina. Furthermore, since activation of Müller glia is associated with numerous retinal diseases, particularly those with associated abnormal neovascularization, these results provide proof-of-concept data supporting the use of activated Müller glia for viral-mediated (GFAP vectors) delivery of various therapeutic gene products to the outer retina using intravitreal injections.

All references cited above are incorporated herein by this reference. The entire contents and drawings of U.S. Provisional Patent Application No. 61/026,990, filed on Feb. 7, 2008 and of U.S. Provisional Patent Application No. 61/093,228, filed on Aug. 29, 2008 are also incorporated herein by this reference.

Although the invention has been described with reference to the above examples, it will be understood that modifications and variations are encompassed within the spirit and scope of the invention. Accordingly, the invention is limited only by the following claims.

What is claimed is:

1. A method of rescuing photoreceptors of the eye in situ comprising:
   a) infecting the retinal ganglion cell (RGC) layer of the retina with a recombinant expression vector that operatively encodes a NT4 growth factor, wherein the vector is administered to the RGC layer by intravitreal delivery into the eye, and wherein the infected cells constitutively express the growth factor, and wherein further outer nuclear layer (ONL) thickness throughout the retina is significantly increased by said administration to the intravitreal layer as compared to outer nuclear layer (ONL) thickness with subretinal injection of the vector; and
   b) administering a calcium channel blocker or a second growth factor selected from BDNF, GDNF, CNTF, βNGF and neurturin (NTN).

2. The method of claim 1, wherein cells neighboring the RGC layer are activated via NT4 expression, which neighboring cells are selected from the group consisting of rod photoreceptors, cone photoreceptors, bi-polar cells, horizontal cells, retinal pigmented epithelial cells, and Müller glia cells.

3. The method of claim 1, wherein the method increases the amplitude of scotopic b-waves, scotopic a-waves, and/or photopic b-waves associated with photoreceptor degeneration in an ocular disease.

4. The method of claim 3, wherein the ocular disease is retinitis pigmentosa or age related macular degeneration.

5. The method of claim 1, wherein the infected RGC layer induces a paracrine response to neighboring cells.

6. The method of claim 1, wherein the expression vector is an AAV vector devoid of viral protein encoding sequences, and wherein the vector comprises nucleic acid sequences encoding NT4.

7. The method of claim 6, wherein the AAV vector is an AAV serotype 2 (AAV2) vector.

8. The method of claim 6, wherein the NT4 gene is flanked by AAV2 inverted terminal repeats (ITR).

9. The method of claim 1, wherein the second growth factor is delivered intravitreally or subretinally.

10. The method of claim 1, wherein the second growth factor is encoded by a recombinant expression vector transduced into a donor cell, which vector is delivered to the eye by implantation of said donor cell therein.

* * * * *